US00PP30186P2

(12) United States Plant Patent
Wood

(10) Patent No.: US PP30,186 P2
(45) Date of Patent: Feb. 12, 2019

(54) ***CYTISUS* PLANT NAMED 'SMNCSCRY'**

(50) Latin Name: *Cytisus scoparius*
Varietal Denomination: SMNCSCRY

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 15/732,300

(22) Filed: Oct. 20, 2017

(51) Int. Cl.
*A01H 5/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — C. A. Whealy

(57) ABSTRACT

A new and distinct cultivar of *Cytisus* plant named 'SMNCSCRY', characterized by its relatively compact and upright to outwardly spreading plant habit; vigorous growth habit; freely branching habit; full and dense plants; freely flowering habit; large bright yellow and red-colored flowers; and good garden performance.

2 Drawing Sheets

Botanical designation: *Cytisus scoparius.*
Cultivar denomination: 'SMNCSCRY'.

BACKGROUND OF THE INVENTION

The present invention relates to a new and distinct cultivar of *Cytisus* plant, botanically known as *Cytisus scoparius*, commonly referred to as Scotch Broom and hereinafter referred to by the name 'SMNCSCRY'.

The new *Cytisus* plant is a product of a planned breeding program conducted by the Inventor in Grand Haven, Mich. The objective of the breeding program is to create new compact and uniform *Cytisus* plants with attractive flower form and color.

The new *Cytisus* plant originated from an open-pollination in 2009 in Grand Haven, Mich. of an unnamed selection of *Cytisus scoparius*, not patented, as the female, or seed, parent with an unknown selection of *Cytisus scoparius* as the male, or pollen, parent. The new *Cytisus* plant was discovered and selected by the Inventor as a single flowering plant from within the progeny of the stated open-pollination in a controlled environment in Grand Haven, Mich. during the spring of 2013.

Asexual reproduction of the new *Cytisus* plant by softwood stem cuttings in a controlled environment in Grand Haven, Mich. since the spring of 2013 has shown that the unique features of this new *Cytisus* plant are stable and reproduced true to type in successive generations.

SUMMARY OF THE INVENTION

Plants of the new *Cytisus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNCSCRY'. These characteristics in combination distinguish 'SMNCSCRY' as a new and distinct *Cytisus* plant:

1. Relatively compact and upright to outwardly spreading plant habit.
2. Vigorous growth habit.
3. Freely branching habit; full and dense plants.
4. Freely flowering habit.
5. Large bright yellow and red-colored flowers.
6. Good garden performance.

Plants of the new *Cytisus* can be compared to plants of the female parent selection. Plants of the new *Cytisus* differ primarily from plants of the female parent selection in the following characteristics:

1. Plants of the new *Cytisus* are denser than plants of the female parent selection.
2. Plants of the new *Cytisus* are more freely flowering than plants of the female parent selection.
3. Plants of the new *Cytisus* have larger flowers than plants of the female parent selection.
4. Plants of the new *Cytisus* and the female parent selection differ in flower color as plants of the female parent selection have yellow-colored flowers.

Plants of the new *Cytisus* can be compared to plants of *Cytisus scoparius* 'Madame Butterfly', not patented. In side-by-side comparisons, plants of the new *Cytisus* differ from plants of 'Madame Butterfly' in the following characteristics:

1. Plants of the new *Cytisus* are more compact and upright than and not as outwardly spreading as plants of 'Madame Butterfly'.
2. Plants of the new *Cytisus* and 'Madame Butterfly' differ in flower color as flowers of plants of 'Madame Butterfly' are lighter yellow in color.

BRIEF DESCRIPTION OF THE PHOTOGRAPHS

The accompanying colored photographs illustrate the overall appearance of the new *Cytisus* plant showing the colors as true as it is reasonably possible to obtain in colored reproductions of this type. Colors in the photographs may differ slightly from the color values cited in the detailed botanical description which accurately describe the colors of the new *Cytisus* plant.

The photograph on the first sheet comprises a side perspective view of a typical flowering plant of 'SMNCSCRY' grown in a container.

The photograph on the second sheet is a close-up view of a typical flowering plant of 'SMNCSCRY'.

DETAILED BOTANICAL DESCRIPTION

The aforementioned photographs and following observations and measurements describe plants grown in three-gallon containers during the spring and summer in a polyethylene-covered greenhouse in Grand Haven, Mich. and under cultural practices typical of commercial *Cytisus* production. Plants were two years old when the photographs and description were taken. During the production of the plants, day temperatures ranged from 18° C. to 27° C. and night temperatures ranged from 5° C. to 10° C. In the following description, color references are made to The Royal Horticultural Society Colour Chart, 2015 Edition, except where general terms of ordinary dictionary significance are used.

Botanical classification: *Cytisus scoparius* 'SMNCSCRY'.

Parentage:

- *Female, or seed, parent*.—Unnamed selection of *Cytisus scoparius*, not patented.
- *Male, or pollen, parent*.—Unknown selection of *Cytisus scoparius*, not patented.

Propagation:

- *Type*.—By softwood stem cuttings.
- *Time to initiate roots, summer*.—About 30 days at temperatures about 20° C.
- *Time to produce a rooted young plant, summer*.—About eight months at temperatures about 20° C.
- *Root description*.—Fine to medium in thickness, somewhat fibrous and fleshy; typically white in color, actual color of the roots is dependent on substrate composition, water quality, fertilizer, substrate temperature and physiological age of roots.
- *Rooting habit*.—Freely branching; dense.

Plant description:

- *Plant form and habit*.—Perennial deciduous shrub; relatively compact and upright to outwardly spreading plant habit; freely branching habit with numerous lateral branches developing per plant; full and dense plant habit; vigorous growth habit.
- *Plant height*.—About 27 cm.
- *Plant diameter*.—About 45 cm.

Lateral branch description:

- *Length*.—About 18 cm.
- *Diameter*.—About 3 mm.
- *Internode length*.—About 6 mm.
- *Strength*.—Strong, flexible.
- *Aspect*.—Upright to about 80° from vertical.
- *Texture*.—Pubescent.
- *Color*.—Close to 137B.

Leaf description:

- *Arrangement*.—Alternate; leaves simple or compound with three leaflets per leaf.
- *Simple leaf length*.—About 7 mm.
- *Simple leaf width*.—About 3 mm.
- *Compound leaf length*.—About 5 mm to 9 mm.
- *Compound leaf width*.—About 2.5 mm.
- *Simple leaf and leaflet shape*.—Obovate.
- *Simple leaf and leaflet apex*.—Acute.
- *Simple leaf and leaflet base*.—Attenuate.
- *Simple leaf and leaflet margin*.—Entire.
- *Simple leaf and leaflet texture, upper and lower surfaces*.—Slightly pubescent.
- *Simple leaf and leaflet venation pattern*.—Pinnate.
- *Simple leaf and leaflet color*.—Developing and fully expanded leaves, upper surface: Close to 137A; venation, close to 137A. Developing and fully expanded leaves, lower surface: Close to 137C; venation, close to 137C.
- *Petioles*.—Length: About 8 mm. Diameter: About 1 mm. Texture, upper and lower surfaces: Pubescent. Color, upper surface: Close to 137A. Color, lower surface: Close to 137C.

Flower description:

- *Flower arrangement and habit*.—Single axillary papilionaceous flowers; flowers face mostly outwardly; freely flowering habit with 100's flowers developing per plant during the flowering season.
- *Natural flowering season*.—Plants flower continuously during the spring in Michigan.
- *Flower longevity on the plant*.—Flowers last about two to three weeks; flowers not persistent.
- *Fragrance*.—None detected.
- *Flower buds*.—Length: About 2 cm. Diameter: About 8 mm. Shape: Spherical. Color: Close to 13A tinged with close to N45D.
- *Flowers*.—Diameter: About 1.4 cm by 2 cm. Depth (height): About 2.5 cm.
- *Corolla*.—Quantity and arrangement: Single whorl of five petals; one larger standard petal, two wing petals and two fused keel petals. Length, standard petal: About 2 cm. Length, wing and keel petals: About 1.8 cm. Width, standard petal: About 1.5 cm. Width, wing and keel petals: About 7 mm. Shape, all petals: Oblong. Apex, all petals: Obtuse. Margin, all petals: Entire. Texture, all petals, upper and lower surfaces: Smooth, glabrous; silky. Color, when opening and fully opened, upper surface: Standard petal: Close to 13A; towards the base, close to N45D. Wing petals: Close to N45A; towards the margins and base, close to 13B. Keel petals: Close to 14D. Color, when opening and fully opened, lower surface: Standard petal: Close to 14C; towards the base, close to N45D. Wing petals: Close to 13C. Keel petals: Close to 14D.
- *Calyx*.—Quantity and arrangement: Two, opposite. Sepal length: About 7 mm. Sepal width: About 4 mm. Sepal shape: Triangular. Sepal apex: Acute. Sepal base: Fused. Sepal margin: Entire. Sepal texture, upper and lower surfaces: Smooth, glabrous. Sepal color, upper and lower surfaces: Close to 184B.
- *Peduncles*.—Length: About 8 mm. Diameter: About 1 mm. Strength: Strong; flexible. Aspect: Erect to about 30° from lateral branch axis. Texture: Smooth, glabrous. Color: Close to 143A.
- *Reproductive organs*.—Stamens: Quantity: About ten. Filament length: About 3.5 mm to 12 mm. Filament color: Close to N155B. Anther length: About 1 mm. Anther shape: Oblong. Anther color: Close to 17A. Pollen amount: Moderate. Pollen color: Close to 17A. Pistils: Quantity: One per flower. Pistil length: About 2.5 cm. Stigma shape: Round. Stigma color: Close to 157A. Style length: About 2.5 mm. Style color: Close to 157A. Ovary color: Close to 191C. Seeds and fruits: Seed and fruit development have not been observed on plants of the new *Cytisus* to date.

Garden performance: Plants of the new *Cytisus* have been observed have good garden performance as exhibited by its tolerance to rain and wind. Plants of the new *Cytisus* have been observed to tolerate temperatures ranging from about −32° C. to about 36° C.

Pathogen & pest resistance: Plants of the new *Cytisus* have not been observed to be resistant to pathogens and pests common to *Cytisus* plants to date.

It is claimed:

1. A new and distinct *Cytisus* plant named 'SMNCSCRY' as illustrated and described.

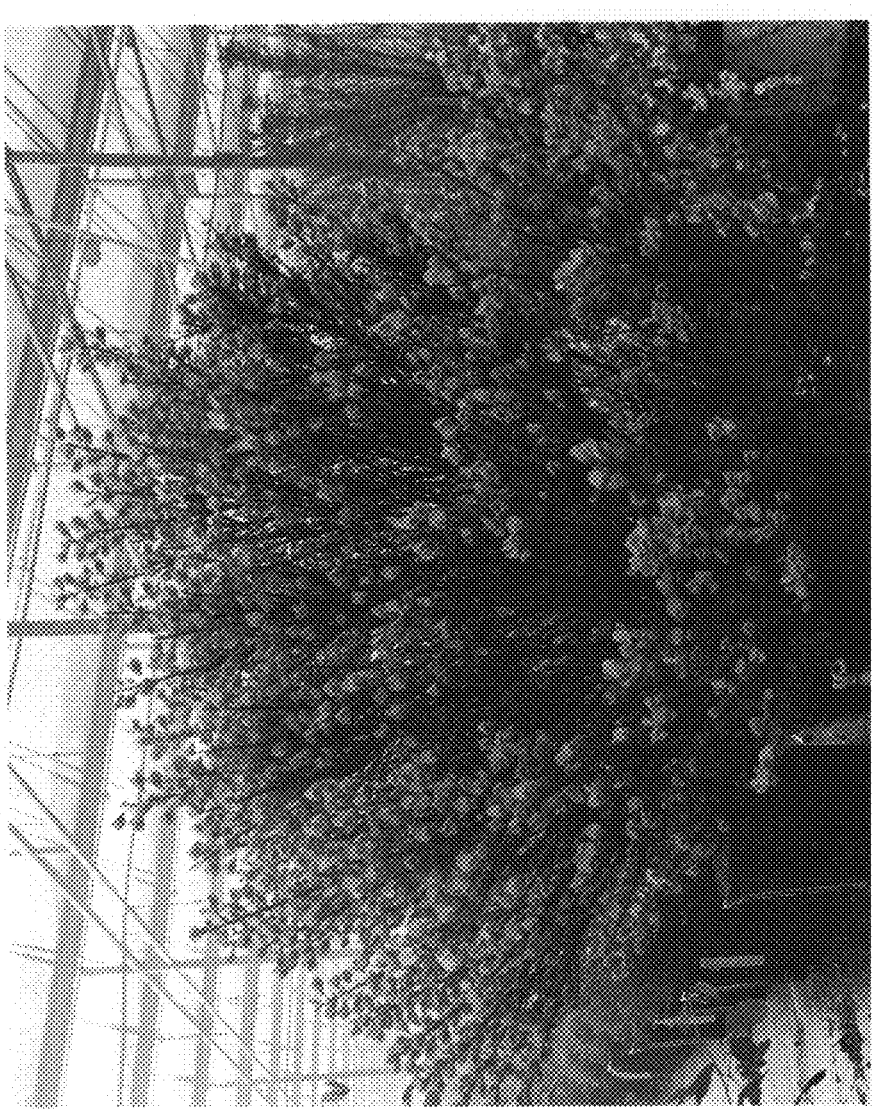

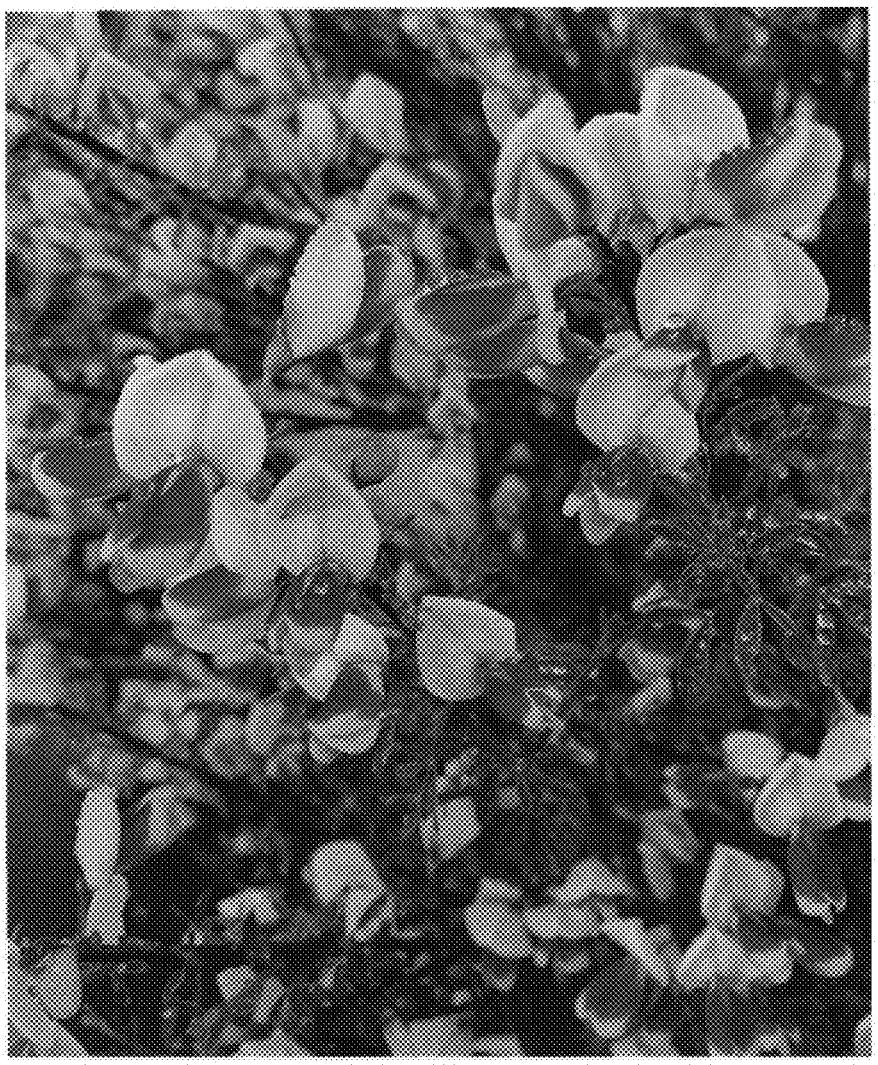

* * * * *